United States Patent
Zhou et al.

(10) Patent No.: US 9,937,077 B2
(45) Date of Patent: *Apr. 10, 2018

(54) PNEUMATIC PRESSURE OUTPUT CONTROL BY DRIVE VALVE DUTY CYCLE CALIBRATION

(71) Applicant: Alcon Research, Ltd., Fort Worth, TX (US)

(72) Inventors: Jiansheng Zhou, Cerritos, CA (US); Kurt D. Leukanech, Laguna Niguel, CA (US); Dan Teodorescu, Fountain Valley, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 649 days.

This patent is subject to a terminal disclaimer.

(21) Appl. No.: 14/325,763

(22) Filed: Jul. 8, 2014

(65) Prior Publication Data

US 2014/0350583 A1    Nov. 27, 2014

Related U.S. Application Data

(63) Continuation of application No. 12/854,281, filed on Aug. 11, 2010, now Pat. No. 8,818,564.

(60) Provisional application No. 61/238,431, filed on Aug. 31, 2009.

(51) Int. Cl.
  *A61F 9/007*  (2006.01)
  *A61B 34/00*  (2016.01)
  *A61B 17/00*  (2006.01)

(52) U.S. Cl.
  CPC .......... *A61F 9/00763* (2013.01); *A61B 34/25* (2016.02); *A61B 2017/00154* (2013.01); *A61B 2017/00176* (2013.01); *A61B 2017/00181* (2013.01); *A61B 2017/00544* (2013.01); *Y10T 83/8858* (2015.04)

(58) Field of Classification Search
  CPC ................. A61F 9/00763; A61B 34/25; A61B 2017/00176; A61B 2017/00544; A61B 2017/00181; A61B 2017/00154; Y10T 83/8858

See application file for complete search history.

(56) References Cited

U.S. PATENT DOCUMENTS

2006/0030951 A1    2/2006    Davlin et al.

*Primary Examiner* — Carlos Ortiz Rodriguez (57) ABSTRACT

In various embodiments, a surgical console may include a pneumatic valve to drive a pneumatic tool coupled to the surgical console. The console may further include a controller operable to control and adjust the valve open/close cycle times according to a valve duty cycle. The valve may switch between ports (valve open time for a first port and valve close time for a second port) such that a total valve time may approximately equal the valve open time plus the valve close time. The valve duty cycle may indicate a percentage of the total valve time for the controller to signal the valve to open and may include an adjustment that corresponds to a signal timing of the open and/or closed valve positions that will result in open and closed operating pressures above a predetermined threshold.

16 Claims, 11 Drawing Sheets

| DIP Switch Settings | Output Voltage | Digital Count | Corresponding Valve Duty Cycle |
|---|---|---|---|
| S1=1; S2=0; S3=0; S4=1; S5=1; S6=0 | 1.674 | 342 | 48.5% |
| S1=1; S2=0; S3=1; S4=0; S5=1; S6=0 | 2.183 | 447 | 49.5% |
| S1=1; S2=1; S3=0; S4=0; S5=1; S6=0 | 2.646 | 541 | 50.5% |

Calibration Table
901

*FIG. 9*

PNEUMATIC PRESSURE OUTPUT CONTROL BY DRIVE VALVE DUTY CYCLE CALIBRATION

PRIORITY CLAIM

This application:

(a) is a continuation application of U.S. patent application Ser. No. 12/854,281 entitled "Pneumatic Pressure Output Control by Drive Valve Duty Cycle Calibration" which was filed Aug. 11, 2010, whose inventors are Jiansheng Zhou, Kurt D. Leukanech, and Dan Teodorescu which is hereby incorporated by reference in its entirety as though fully and completely set forth herein, and (b) claims the benefit of priority of U.S. Provisional Application Ser. No. 61/238,431 (U.S. patent application Ser. No. 12/854,281 claimed the benefit of priority of provisional application Ser. No. 61/238,431 entitled "Pneumatic Pressure Output Control by Drive Valve Duty Cycle Calibration" filed on Aug. 31, 2009, whose inventors are Jiansheng Zhou, Kurt D. Leukanech, and Dan Teodorescu), which is also hereby incorporated by reference in its entirety as though fully and completely set forth herein.

FIELD OF THE INVENTION

The present invention generally pertains to calibration. More particularly, but not by way of limitation, the present invention pertains to calibration for a pneumatic surgical system.

DESCRIPTION OF THE RELATED ART

Vitreo-retinal procedures include a variety of surgical procedures performed to restore, preserve, and enhance vision. Vitreo-retinal procedures are appropriate to treat many serious conditions of the back of the eye. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

The vitreous is a normally clear, gel-like substance that fills the center of the eye. It makes up approximately ⅔ of the eye's volume, giving it form and shape before birth. Certain problems affecting the back of the eye may require a vitrectomy, or surgical removal of the vitreous.

A vitrectomy may be performed to clear blood and debris from the eye, to remove scar tissue, or to alleviate traction on the retina. Blood, inflammatory cells, debris, and scar tissue obscure light as it passes through the eye to the retina, resulting in blurred vision. The vitreous is also removed if it is pulling or tugging the retina from its normal position. Some of the most common eye conditions that require vitrectomy include complications from diabetic retinopathy such as retinal detachment or bleeding, macular hole, retinal detachment, pre-retinal membrane fibrosis, bleeding inside the eye (vitreous hemorrhage), injury or infection, and certain problems related to previous eye surgery. Vitrectomies may be performed in the anterior or posterior portions of the eye. While an anterior vitrectomy may be a planned procedure performed in such settings as traumatic cataract removal or secondary IOL (intraocular lens) placement, an anterior vitrectomy is most often an unplanned addition to a cataract surgery when vitreous is inadvertently prolapsing into the anterior segment after a rupture of the posterior capsule.

The retinal surgeon performs a vitrectomy with a microscope and special lenses designed to provide a clear image of the back of the eye. Several tiny incisions just a few millimeters in length are made on the sclera. The retinal surgeon inserts microsurgical instruments through the incisions such as a fiber optic light source to illuminate inside the eye, an infusion line to maintain the eye's shape during surgery, and instruments to cut and remove the vitreous.

In a vitrectomy, the surgeon creates three tiny incisions in the eye for three separate instruments. These incisions are placed in the pars plana of the eye, which is located just behind the iris but in front of the retina. The instruments which pass through these incisions include a light pipe, an infusion port, and the vitrectomy cutting device. The light pipe is the equivalent of a microscopic high-intensity flashlight for use within the eye. The infusion port is required to replace fluid in the eye and maintain proper pressure within the eye. The vitrector, or cutting device, works like a tiny guillotine, with an oscillating microscopic cutter to remove the vitreous gel in a controlled fashion. This prevents significant traction on the retina during the removal of the vitreous humor.

The surgical machine used to perform a vitrectomy and other surgeries on the anterior and/or posterior of the eye is very complex. Typically, such an ophthalmic surgical machine includes a main console to which the numerous different tools are attached. The main console provides power to and controls the operation of the attached tools. The main console may also be used for performing other ophthalmic procedures such as phacoemulsification.

The attached tools typically include probes, scissors, forceps, illuminators, vitrectors, and infusion lines. Each of these tools is typically attached to the main surgical console. A computer in the main surgical console monitors and controls the operation of these tools. These tools also get their power from the main surgical console. Some of these tools are electrically powered while others are pneumatically powered.

In order to provide pneumatic power to the various tools, the main surgical console has a pneumatic or air distribution module. This pneumatic module conditions and supplies compressed air or gas to power the tools. Typically, the pneumatic module is connected to a cylinder that contains compressed gas. The pneumatic module may provide the proper gas pressure to operate the attached tools properly.

SUMMARY OF THE INVENTION

In various embodiments, a surgical console may include a pneumatic valve (e.g., a four way solenoid valve) with at least two ports operable to alternately provide pressurized gas to drive a pneumatic tool (such as a vitrectomy probe) coupled to the surgical console. The surgical console may further include a controller operable to control and adjust the valve open/close times according to a valve duty cycle. The valve may switch between ports (valve open time for a first port and valve close time for a second port) such that a total valve time may approximately equal the valve open time plus the valve close time. The valve duty cycle may indicate a percentage (e.g., 50%) of the total valve time for the controller to signal the valve to open.

Because different valve open/close timings can lead to a loss in operating pressure, an adjustment may be made to the valve duty cycle so that signal timing for the open and/or closed valve positions will result in open and closed operating pressures above a predetermined threshold. For example, the adjusted valve duty cycle may be approximately equal to a previous valve duty cycle+(((abs(open pressure)−abs(closed pressure))/2)*(valve duty cycle delta/differential pressure change delta)) where the previous valve duty cycle is the valve duty cycle during testing, open pressure and closed pressure are differential pressures for the ports at respective open and closed times during one cycle of the valve, and the valve duty cycle delta/differential pressure change delta is a ratio of valve duty cycle change to resulting differential pressure change (for example, in the valve open pressure). For calculating the new valve duty cycle, the open pressure and closed pressure for the port may be taken during a lowest performance point for the pneumatic system (e.g., when the absolute pressure difference between the open pressure and closed pressure is the lowest such that (abs(open pressure)+abs(closed pressure)) is at a minimum for the measured pressure data). Once determined, the valve duty cycle may be stored on a memory accessible by the controller for future use.

In some embodiments, a valve duty cycle may be input into the system through a series of DIP switch settings. For example, the surgical console may include DIP switches and resistors coupled together such that the DIP switches are configurable to combine one or more of the resistors in a resistor network. The DIP switches may be set such that upon applying an input voltage to the resistor network, an output voltage of the resistor network is indicative of a valve duty cycle. In some embodiments, the surgical console may include an analog to digital converter operable to convert the output voltage to a digital value that software executing on the surgical console can use to determine a valve duty cycle (e.g., through the use of a look-up table that associates the digital value with an associated valve duty cycle).

BRIEF DESCRIPTION OF THE DRAWINGS

For a more complete understanding of the present invention, reference is made to the following description taken in conjunction with the accompanying drawings in which:

FIGS. 5a-6 illustrate various embodiments of a DIP switch and resistor network;

It is to be understood that both the foregoing general description and the following detailed description are exemplary and explanatory only and are intended to provide a further explanation of the present invention as claimed.

DETAILED DESCRIPTION OF THE EMBODIMENTS

U.S. Patent Application Publication entitled "Pneumatic System for a Vitrector," Publication No. 20080149197, Ser. No. 11/614,678, by Denis Turner, Robert Palino, Argelio Olivera, and Mark Hopkins filed Dec. 21, 2006 is hereby incorporated by reference in its entirety as though fully and completely set forth herein.

Figure 1:
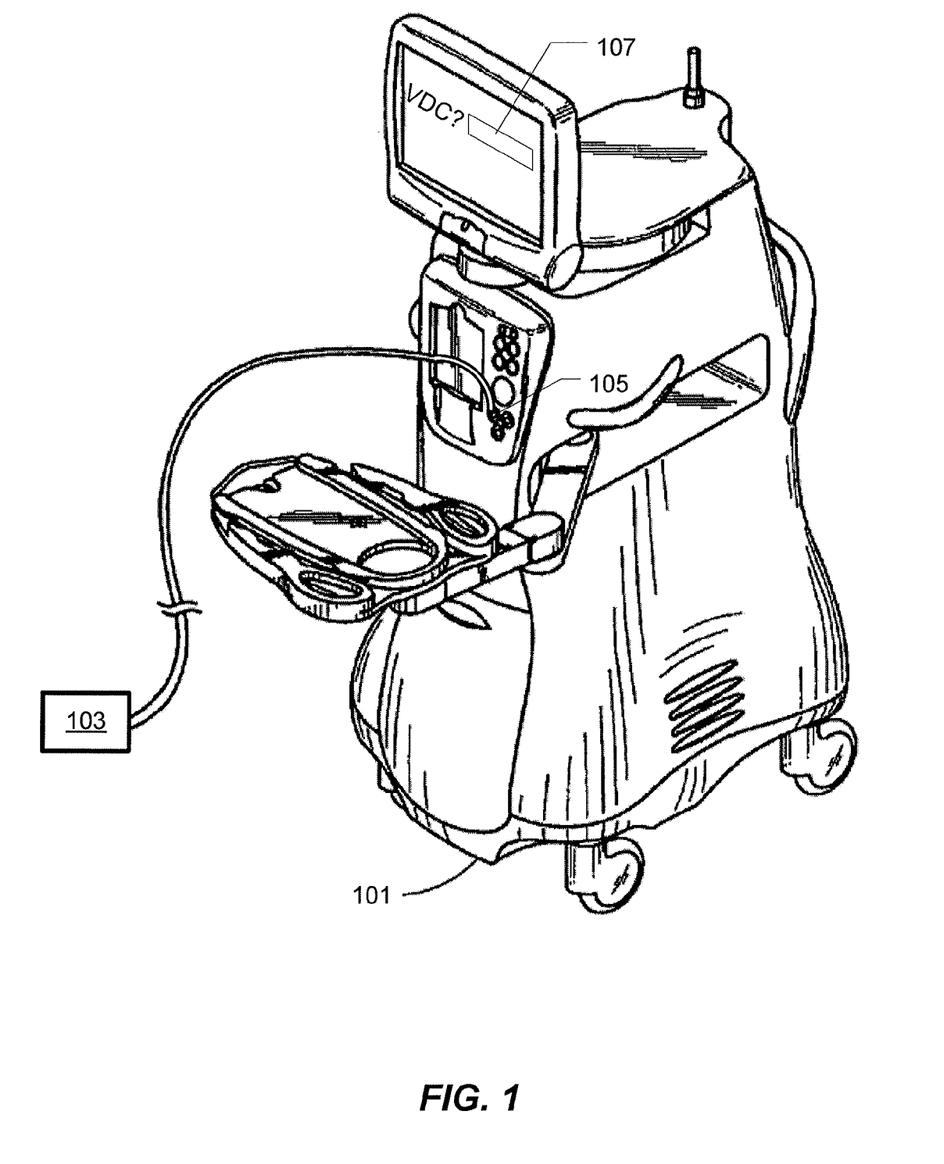
FIG. 1 illustrates a surgical console, according to an embodiment.

FIG. 1 illustrates an embodiment of a surgical console 101 for a pneumatically powered ophthalmic surgical machine. The surgical console 101 may operate to assist a surgeon in performing various ophthalmic surgical procedures, such as phacoemulsification and vitrectomy. The surgical console 101 may include an internal monitor system, one or more controllers (e.g., proportional controllers), and tools (which may include phacoemulsification tools and/or pneumatic tools 103). The pneumatic tools 103 may include, for example, scissors, vitrectors, forceps, and injection or extraction modules. Other tools 103 may also be used. A compressed gas, such as nitrogen, may provide the power for pneumatic tools 103. The compressed gas may pass through the gas pressure monitor system, through one or more manifolds to the one or more proportional controllers, and through additional manifolds and/or tubing to tools 103.

Figure 2:
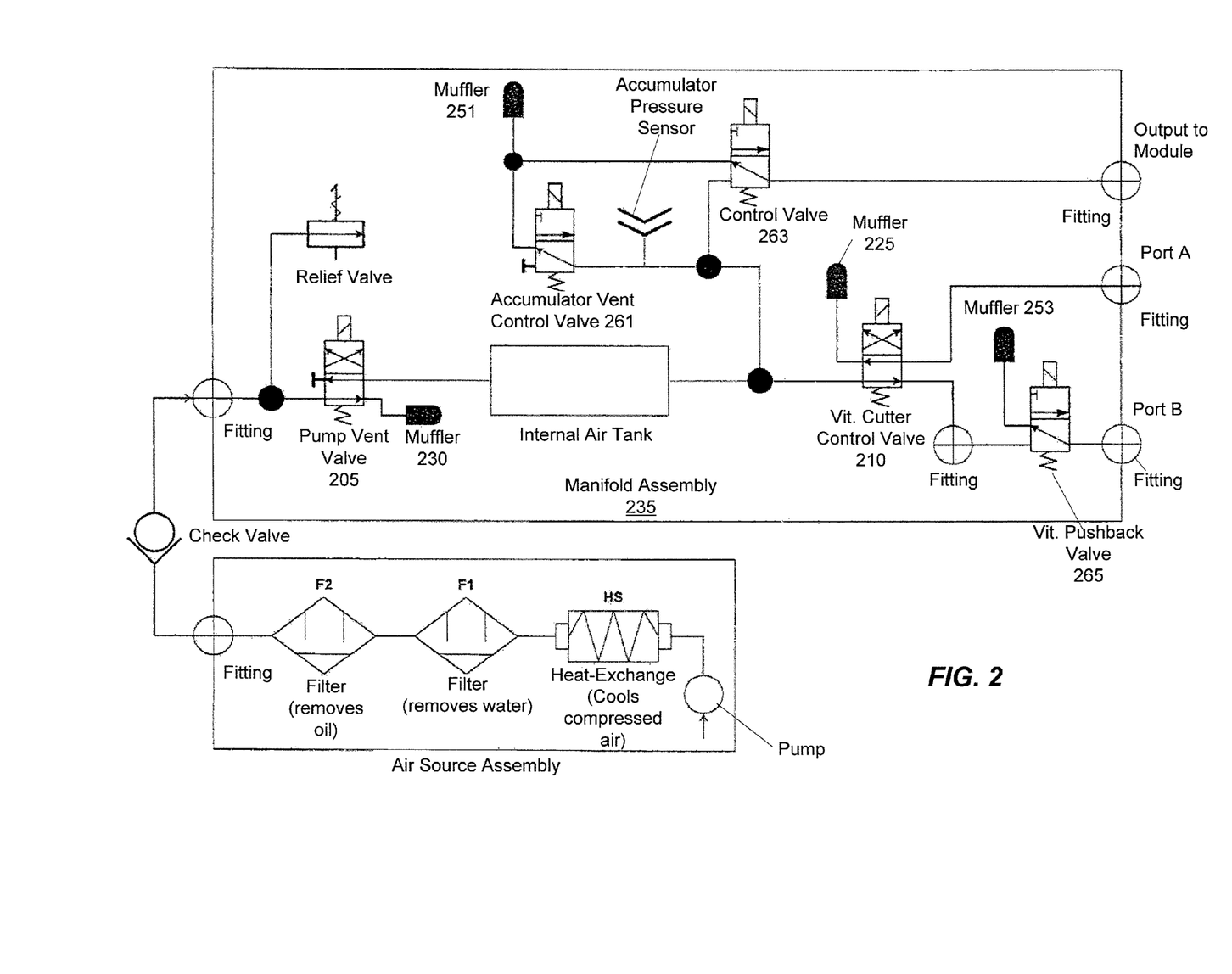
FIG. 2 illustrates a diagram of a pneumatic system, according to an embodiment.

FIG. 2 is a schematic of a pneumatic system for a pneumatically powered vitrectomy machine, according to an embodiment. In FIG. 2, the pneumatic system may include pump vent valve 205, output valve 210, mufflers 225, 230, 251, 253, manifold 235, and output ports A and B for respective pneumatic channels to power a pneumatic tool 103 (e.g., see FIG. 4).

In some embodiments, pump vent valve 205 may be a four-way valve. Valve 205 may include a solenoid that operates to move the valve to one of at least two positions. In one position, pressurized gas may pass through pump vent valve 205 and out of muffler 230. In another position, pump vent valve 205 may allow pressurized gas to pass through pump vent valve 205 to provide power to the tool 103. Pump vent valve 205 may be controlled by a controller (e.g., controller 300 as seen in FIG. 3).

In some embodiments, output valve 210 may be a four-way valve. Valve 210 may include a solenoid that operates to move the valve to one of at least two positions. In one position, the valve 210 may provide pressurized gas to output port A and vent pressurized gas from output port B (i.e., the "closed" position). In this position, pressurized gas can pass through output valve 210 to output port A where the pressurized gas provides pneumatic power to tool 103. Pressurized gas may also pass through output valve 210 and muffler 225 where it is exhausted to the atmosphere. In another position (i.e., the "open" position), output valve 210 allows pressurized gas to pass to output port B through valve 265 where the pressurized gas provides pneumatic power to tool 103. Pressurized gas may also pass through output valve 210 to muffler 225 where it is exhausted to the atmosphere. Output valve 210 may also be controlled by controller 300. In some embodiments, the controller 300 may signal the solenoid valve to close during the closed position (a solenoid may act to move the valve to divert air through port A) and, upon discontinuing the signal (or sending an open signal), a spring (or other actuating mechanism) may return the valve to the open position (in which the valve is in a position to divert air to port B). During a valve duty cycle of 50%, the controller may apply the close signal for approximately the same amount of time that the signal is discontinued (the open position) or an open signal is applied.

In some embodiments, manifold assembly 235 may be machined out of a metal, such as aluminum, or plastic. Other materials are also contemplated. Manifold assembly 235 may be air tight, contain various fittings and couplings, and may be designed to withstand relatively high gas pressures. Manifold assembly 235 may be manufactured as a collection of individual pieces or may be manufactured as a single piece. For example, manifold assembly 235 may be machined from a single piece of aluminum. Mufflers 225, 230, 251, and 253 may suppress noise made by escaping gas.

Figure 3:
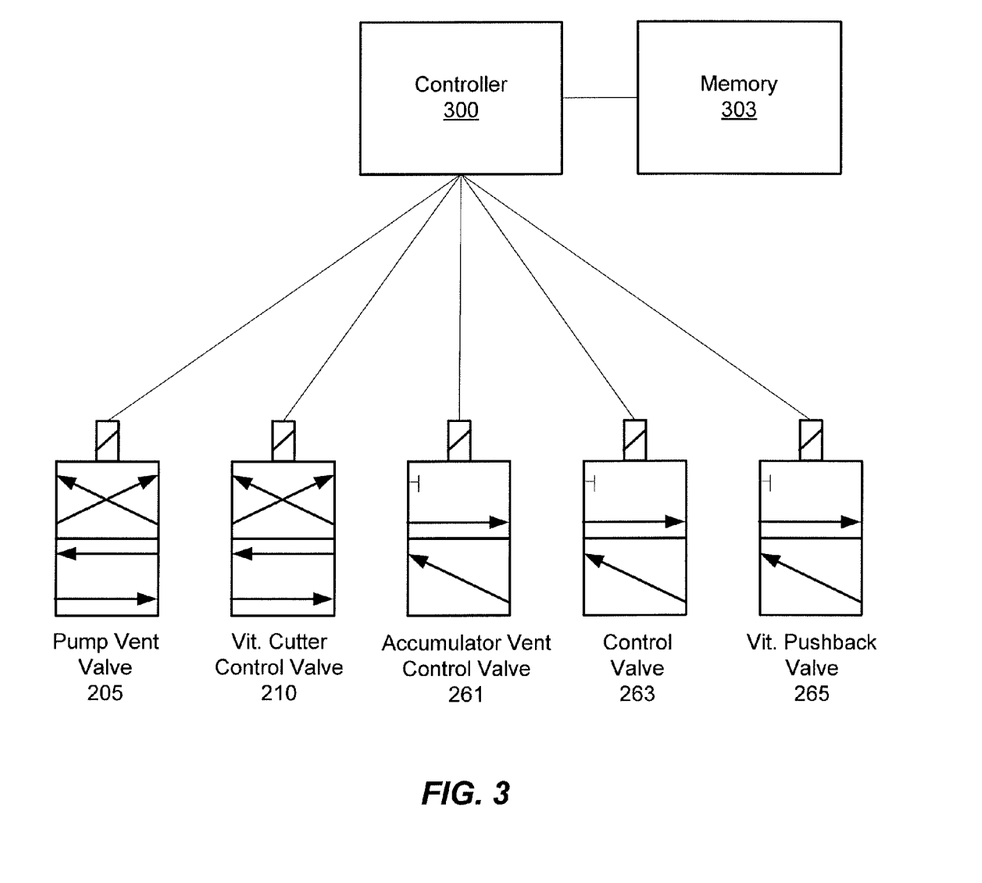
FIG. 3 illustrates a controller for the pneumatic valves, according to an embodiment.

FIG. 3 illustrates a schematic of a controller 300 and valves 205, 210, 261, 263, and 265 for a pneumatically powered vitrectomy machine, according to an embodiment. In some embodiments, controller 300 may send control signals to valves 205, 210, 261, 263, and 265 via interfaces coupling the valves to the controller. Interfaces may include electrical conductors such as wires, buses, traces, etc. Controller 300 may be an integrated circuit capable of performing logic functions. Controller 300 may include an integrated circuit package with power, input, and output pins. In various embodiments, controller 300 may be a valve controller or a targeted device controller. In such a case, controller 300 may perform specific control functions targeted to a specific device, such as a valve. In some embodiments, controller 300 may be a microprocessor. Controller 300 may be programmable so that it can function to control valves as well as other components of the machine. In some embodiments, controller 300 may be a special purpose controller configured to control different valves that perform different functions.

Figure 4:
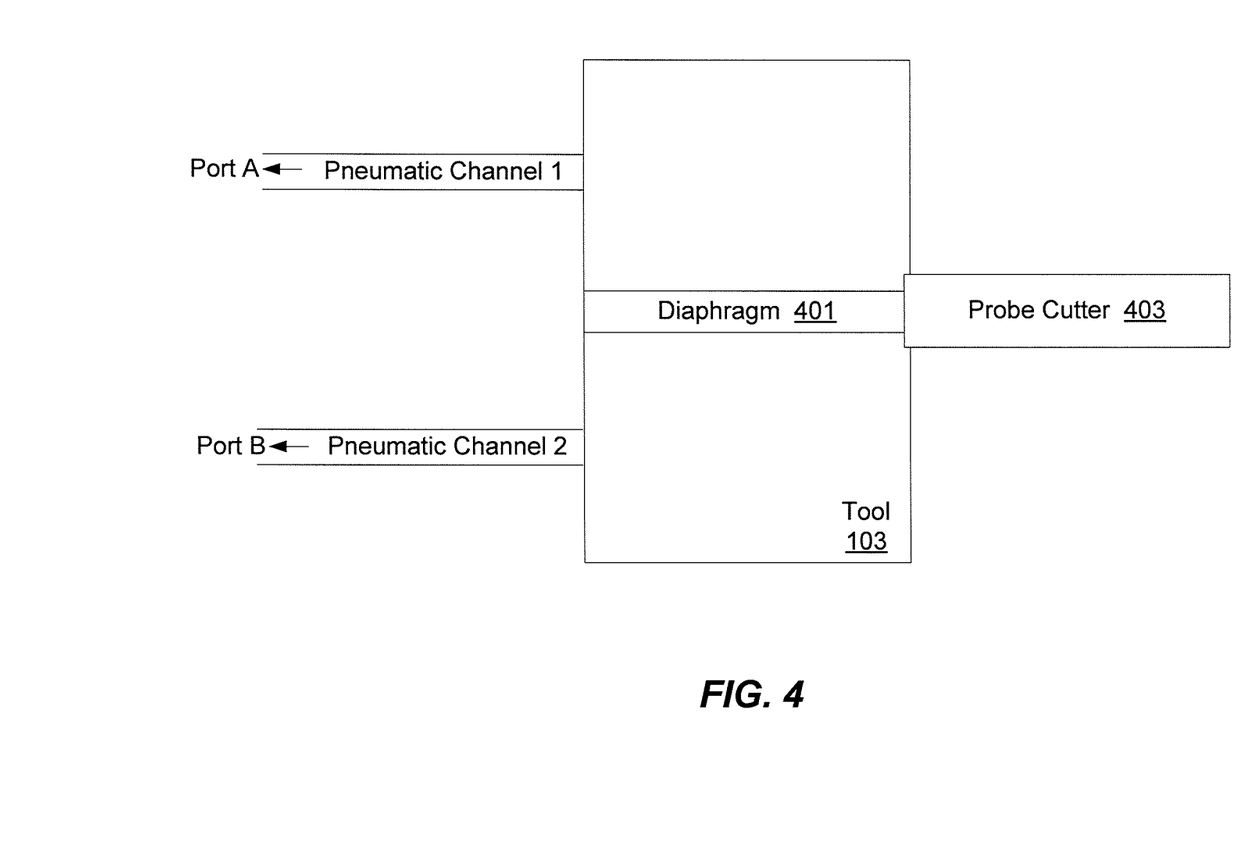
FIG. 4 illustrates a diagram of an embodiment of a pneumatic tool.

FIG. 4 illustrates an embodiment of a tool 103 (such as a vitrector) that may be attached to output ports A and B to act as a cutting device. The cutter 403 may be moved by a cylinder that in turn is moved by pressurized gas. The cylinder may oscillate as pressurized gas is alternately directed to output ports A and B. Such a vitrectomy device may be designed to operate at various cut rates (e.g., 1000 cuts per minute, 2500 cuts per minute, 5,000 cuts per minute, etc). Other cut rates are also contemplated. Port A and Port B may provide separate pneumatic channels (and a differential pressure between the two channels) for driving a tool 103. Alternating pressure pulses may be generated by a four way solenoid valve (e.g., vitrectomy cutter control valve 210) cycling pressure output between the two channels. As seen in FIG. 4, the pressure differential may move a diaphragm 401 reciprocally inside the tool 103 (e.g., a probe) to move the linked probe cutter 403 on tool 103. A pressure bias in the two pneumatic channels (e.g., resulting in a higher pressure differential in either the open or close position of the valve) may affect the function and/or performance of the tool 103. Because of various factors (e.g., valve to valve variations and flow restriction/resistance variations in the two channels from console to console), pressure differentials may vary between different valves 210 in different consoles 101 resulting in difficulty providing a consistent operating pressure differential. To control the pressure differentials of the two pneumatic channel output, software may be used to control the solenoid valve 210 open/closed timing (also known as the valve duty cycle). The valve duty cycle may be adjusted through calibration to better balance the differential pressure during both the open/closed positions of the valve. By adjusting the valve duty cycle, the time for delivering pressurized air to each pneumatic channel in a valve open/closed cycle may be lengthened or shortened to achieve a more consistent differential pressure throughout the valve cycle for smoother tool operation.

For example, at 2500 cuts per minute probe rate, valve 210 may provide pressurized air alternately to port A and port B at a rate of approximately 24 ms per cycle. To obtain a cut rate of 2500 cuts per minute, the two pneumatic channels may cycle on/off every 24 ms (2500 cuts/min or 1 min/2500 cuts*60 seconds/1 min=0.024 seconds/cut=24 ms/cut), which may open for 12 ms to each channel. In some embodiments, a transition time to actually open and close the channels may use part of the cycle time. For example, pneumatic channel 1 (i.e., via port A of control valve 210) may take 4 ms to open (while pneumatic channel 2 is closing) and 2 ms to close (while pneumatic channel 2 is opening) for a total transition time per 24 ms cycle of 6 ms. Other transition times are also contemplated. Because of the transition time, the valve may actually be open only 8 ms (12 ms−4 ms) to channel 1 while closed to channel 2 and may be closed for 10 ms (12 ms−2 ms) to channel 1 while open to channel 2. This valve timing difference of 8 ms vs. 10 ms in providing pressurized air to channel 1 and channel 2 can result in an unbalanced pressure differential in the two channels. In some embodiments, it may be desirable for the open time durations of the two channels to be approximately the same (e.g., in the case of 2500 cuts/minute, actually open for approximately (24 ms−6 ms)/2=9 ms). If the transition timings are constant for all valves 210 then software control may adjust the valve duty cycle to achieve approximately equal actual open time durations for both channels. In this example, software may adjust the nominal open time to 13 ms for channel 1 and 11 ms for channel 2. Thus, for this example, excluding transition time, the actual open time of channel 1 may be 13 ms−4 ms=9 ms and the actual open time of channel 2 may be 11 ms−2 ms=9 ms (similar to channel 1). However, because the transition time may vary between various valves 210 (e.g., due to manufacturing variances in the valve 210), a fixed timing offset may not successfully counter the imbalance. For example, a different valve may take 3 ms (instead of 4 ms) to open channel 1 (while pneumatic channel 2 is closing) and 2 ms to close channel 1 (while pneumatic channel 2 is opening). Applying the same software control valve duty cycle (e.g., 13 ms nominal open time for channel 1 and 11 ms nominal open time for channel 2), the actual open time for pneumatic channel 1 may be 13 ms−3 ms=10 ms and the actual open time for channel 2 may be 11 ms−2 ms=9 ms. Therefore, in this example, pneumatic channel 1 may remain actually open 1 ms or 11% longer than pneumatic channel 2. The difference may result in an uneven power balance between the two pneumatic channels which may result in a lower effective cutting rate/power. Similarly a fixed timing offset may not successfully counter the imbalance caused by the flow restriction/resistance variations in the two channels from console to console.

In some embodiments, a valve duty cycle may be adjusted for individual valves and or console bases (e.g., to compensate for the different transition times of various valves and flow restriction/resistance variations of various consoles). By applying an adjusted valve duty cycle to the cycle times for the pneumatic channels, the pneumatic channels may be actuated during the total cycle time to have approximately equal actual open times. As noted above, a 50% valve duty cycle may correspond to applying a signal to close the valve for approximately the same amount of time as the signal is not applied (corresponding to the open position). An adjustment of 1% may result in a 51% valve duty cycle that corresponds to applying a signal to close the valve for approximately 51% of the total cycle time (and 49% of the total time no signal (or an open signal) is applied to open the valve). The longer 51% valve duty cycle may thus compensate, for example, for a valve that takes longer to close than it does to open and or a console that has higher flow restriction/resistance in the channel connecting to close position of the valve.

In some embodiments, a valve duty cycle value for the valve 210 may be stored in a memory 303 on the console 101 or tool 103. The memory 303 may include a DIP switch (a dual in-line package switch), a variable resistor, digital potentiometer, or an EEPROM (electrically erasable programmable read-only memory). In some embodiments, the valve duty cycle may be determined through trial and error and may be programmed or written into the memory 303 (e.g., at manufacture) or may be received, for example, through user interaction with the console 101 (e.g., as a value entered into a graphical user interface 107 of the console 101). The valve duty cycle may then be used by the surgical console 101 (e.g., controller 300 in surgical console 101) to control the open/close times of the valve 210.

Figure 5A:
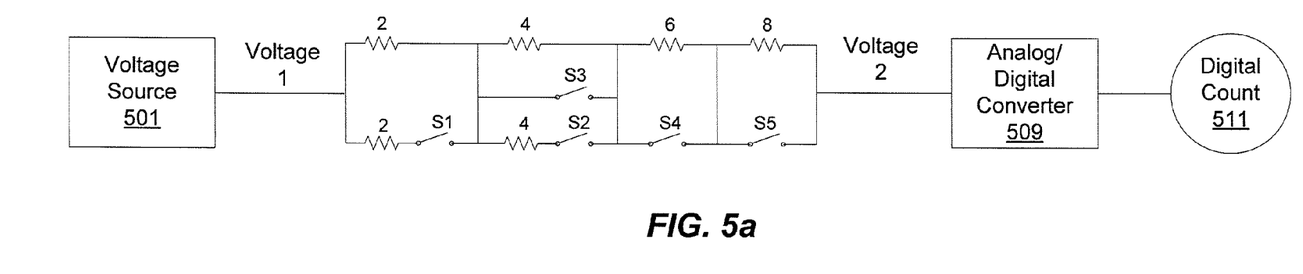
Figure 5C:
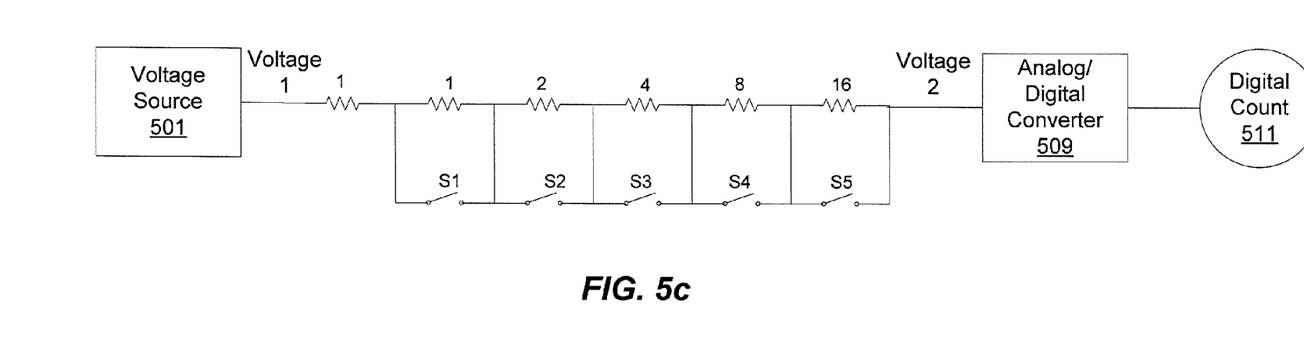
Figure 5D:
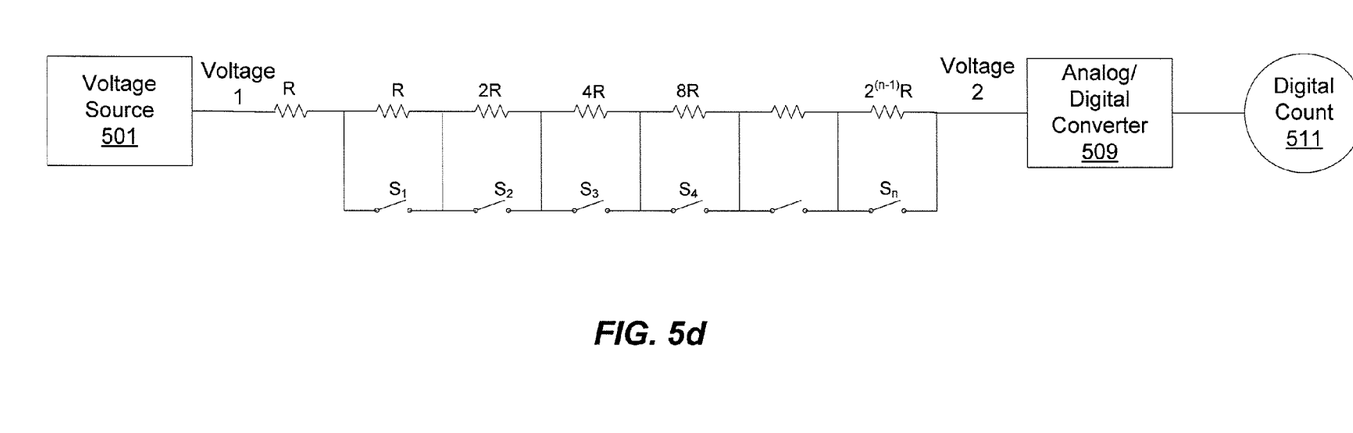
Figure 6:
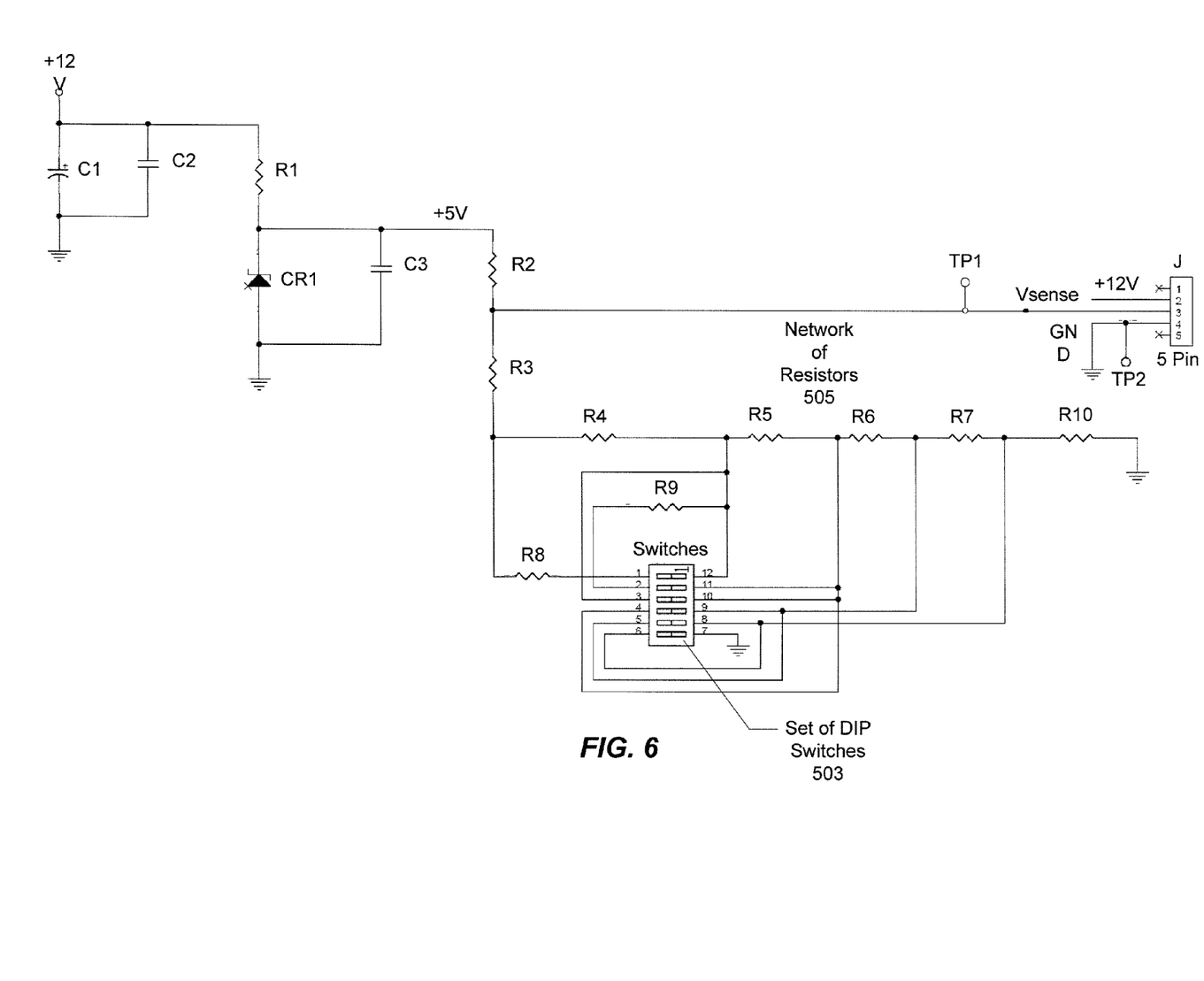

As seen in FIG. 5a-6, one or more DIP switches S1, S2, S3, etc. may be connected to a network of resistors (each of which may have a different resistance). FIGS. 5a and 5c illustrate embodiments with 5 DIP switches and FIGS. 5b and 6 illustrate embodiments with 6 DIP switches. FIG. 5d illustrates an embodiment with n DIP switches. Each DIP switch may be programmed with a 1 or 0 (switch on or off) to allow current through its corresponding resistor or to block current from its corresponding resistor. The network of resistors and DIP switches may have a total resistance that is based on the DIP switch settings. For example, with 6 DIP switches (each with a corresponding resistor), the network of resistors may be configured to have a resistance selected from $2^6=64$ possible resistances. Combinations of the DIP switch settings may therefore produce different resistant values of the resistor network. For example, above each resistor in FIGS. 5a-6 are example resistance multiples (e.g., in kilohms) (other resistances are also possible). As seen in FIG. 5a, example network resistances may be 1, 2, 3, 4, 5, 6, 7, 8, 9, 10, 11, 12, 13, 14, 15, 16, 17, 18, 19, or 20 based on the settings of the 5 DIP switches (in the configuration shown, 32 DIP switch combinations may produce 20 network resistance values in increments of 1 along with 12 duplicates). Other configurations are also possible (e.g., different resistance values, different DIP switch placements, etc). In the embodiment shown in FIG. 5b, 64 DIP switch combinations may produce 40 network resistance values in increments of 0.5 along with 24 duplicates (e.g., network resistance values or 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, and 20.5). As seen in FIG. 5c, 5 DIP switch resistor network may include 32 DIP switch combinations to produce 32 network resistance values in increments of 1 without duplicates (e.g., resistance values of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, and 32). As seen in FIG. 5d, an n DIP switch resistor network may include $2^n$ DIP switch combinations to produce $2^n$ network resistance values in increment of R without duplicates (e.g., resistance values are R, 2R, 3R, 4R, 5R, . . . , $2^n$R). A known voltage (e.g., 5 volts) may be applied to the resister network (e.g., by voltage source 501) and a resulting voltage may be converted to a digital count 511 by an analog/digital converter 509. Software executing on the surgical console may use the digital count 511 to determine a corresponding valve duty cycle. For example, a table lookup may be performed on the digital count to determine a corresponding valve duty cycle value. In some embodiments, a calibration table 901 (e.g., see FIG. 9) may be stored on the console with digital counts and corresponding valve duty cycle values.

Figure 9:
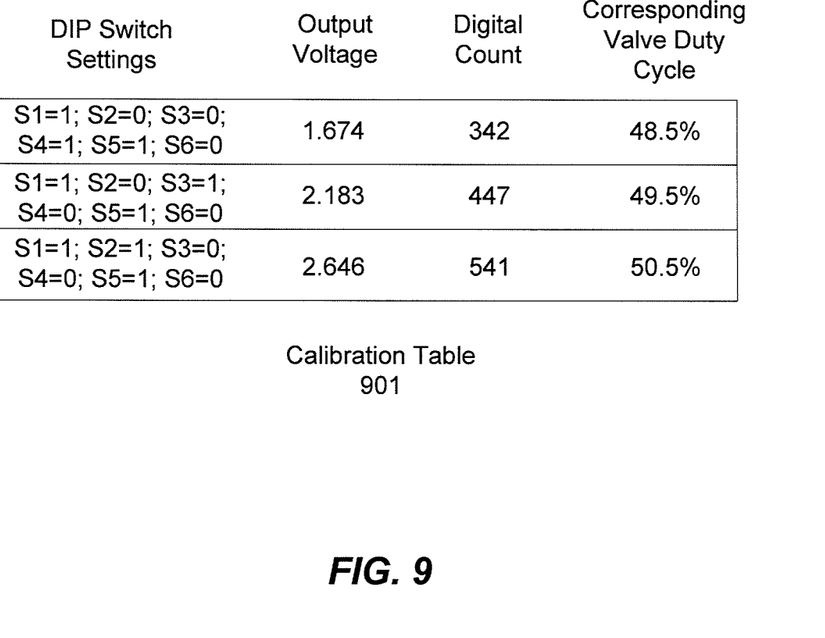
FIG. 9 illustrates a calibration table, according to an embodiment.

As noted above, the DIP switches (e.g., in the set of DIP switches 503) may be programmed in various on/off (1/0) positions to combine selected resistances in the network of resistors 505. The network of resistors may act as a voltage splitter to output a second voltage as a result of the first voltage applied to the network. The ADC 509 may convert the second voltage into a digital count 511. For example, Voltage 2 may result in a digital count of 447 (e.g., corresponding to a voltage of 2.183 Volts). Software executing on the surgical console may use the digital count of 447 to determine a corresponding valve duty cycle (in this case 49.5%). For example, as seen in FIG. 9, a look-up table may be accessed to determine a valve duty cycle corresponding to the digital count. In some embodiments, the valve duty cycle may be determined and stored in a writable memory (e.g., an EEPROM). During subsequent uses of the surgical consoles, the EEPROM may be read instead of determining the valve duty cycle through use of the DIP switches. Using the EEPROM for subsequent uses may allow for a quicker determination of the valve duty cycle. Using the EEPROM may also prevent false values associated with the DIP switches being inadvertently switched or bumped or set by unauthorized personnel. In some embodiments, a new valve duty cycle may be read into the EEPROM when the surgical console receives an indication that a new value is being determined (e.g., a user may enter a password in the user interface to authenticate the user and set the console for receiving a new valve duty cycle or a user may set a switch or press a button near the DIP switches indicating to the surgical console to detect and store a new valve duty cycle in the EEPROM (e.g., as determined from the DIP switches).

Figure 7:
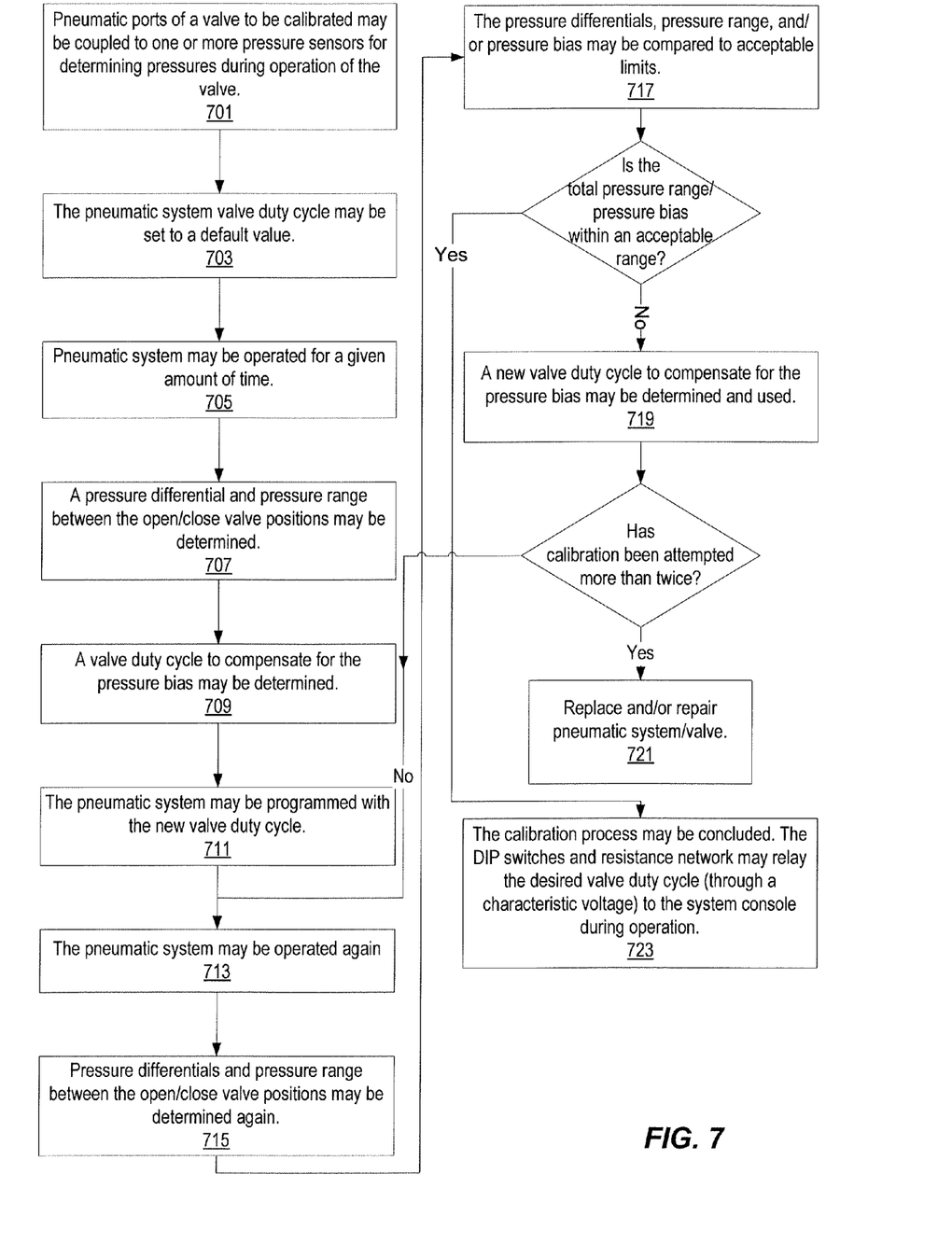
FIG. 7 illustrates a flowchart of a method for calibrating a pneumatics system, according to an embodiment.

FIG. 7 illustrates a method for determining a valve duty cycle for calibrating valve 210. The elements provided in the flowchart are illustrative only. Various provided elements may be omitted, additional elements may be added, and/or various elements may be performed in a different order than provided below.

At 701, pneumatic ports of a valve 210 to be calibrated may be coupled to one or more pressure sensors for determining the pressure of each port (or a differential pressure between the ports) during operation of the valve 210. For example, separate pressure sensors may be coupled to each port (A and B) or a differential pressure sensor may be coupled to both ports A and B. If using separate pressure sensors on each port, a differential pressure may be calculated using the pressure data from each port. As seen in FIG. 1, tool 103 may be a pressure transducer box with the one or more pressure sensors coupling to the A and/or B ports through ports 105. In some embodiments, the valve 210 may be tested while coupled to the surgical console (e.g., the pressure sensors may be coupled to the output pneumatic ports 105 of the surgical console 101). In some embodiments, a cuts per minute setting may be set for the valve (e.g., 2500 cuts per minute).

At 703, the pneumatic system valve duty cycle may be set to a default value (e.g., the calibration DIP switches may be set to 50% valve duty cycle which may result in no applied offset to the open/close valve timing). The DIP switch settings may be set using a calibration table 901 that relates DIP switch settings to valve duty cycles.

At 705, pneumatic system (including valve 210) may be operated for a given amount of time (e.g., 10 seconds). During the pneumatic system operation, pressure data for the run may be detected through the pressure sensors. In some embodiments, a footswitch treadle may be depressed to activate the pneumatic system. In some embodiments, the pneumatic system may be operated for an extended time (e.g., 1 to 2 hours) especially if the pneumatic system and/or console is new. The extended operation prior to calibration may allow the system and/or console to settle out initial valve variations due to manufacturing, friction points, and other component interaction points (e.g., initial friction on new parts may be worn down as the new part interacts with other parts for the extended period). In some embodiments, the pneumatic system may be discontinued after the initial run and then operated again for another set amount of time (e.g., 5 to 10 seconds) before taking the pressure data. In some embodiments, a wait time (e.g., 5 to 10 seconds) may be applied between pneumatic system runs.

Figure 8A:
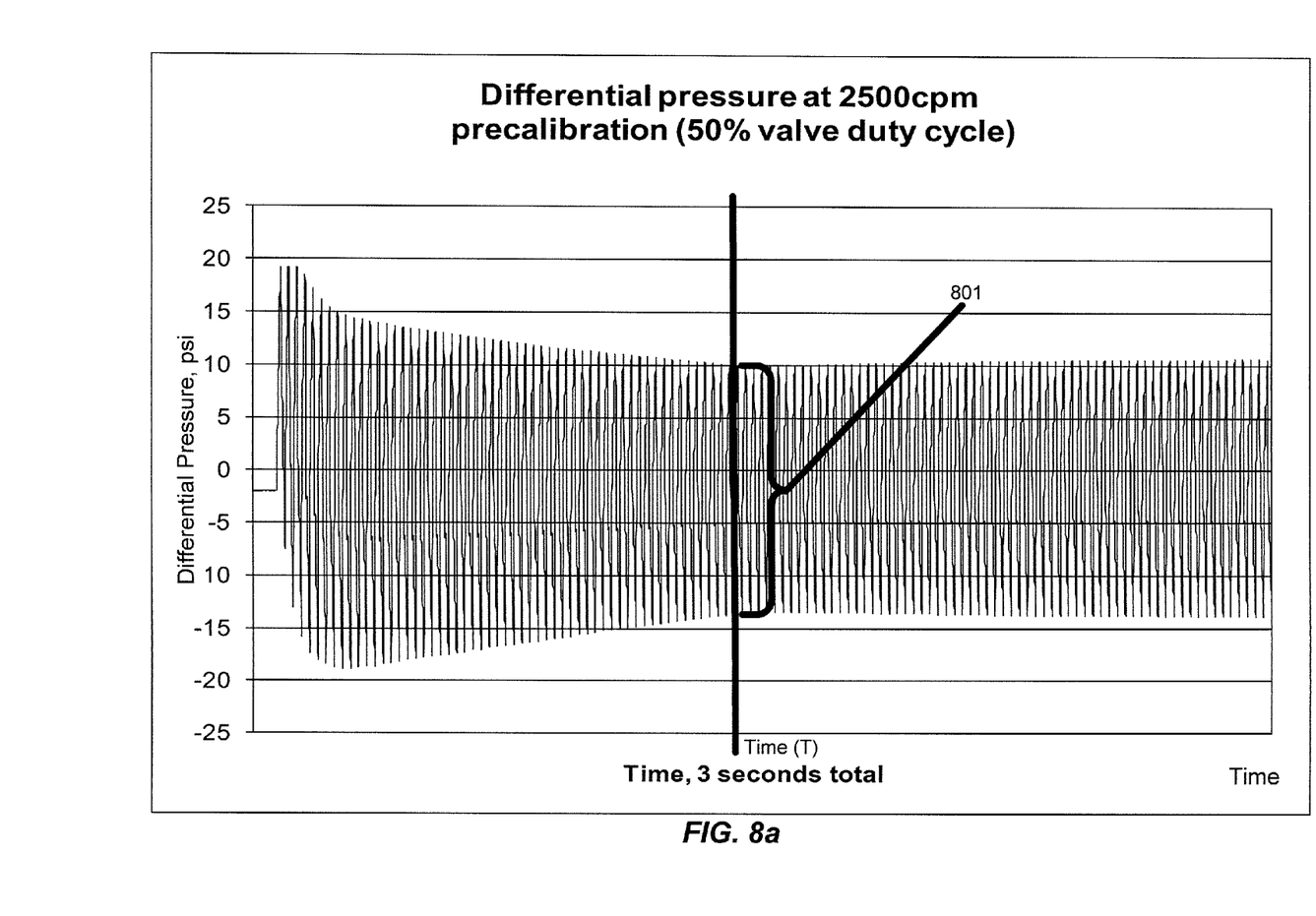
FIGS. 8a-8b illustrate pressure data for a pneumatic valve, according to an embodiment.

At 707, pressure differentials and pressure range between the open/close valve positions may be determined. FIG. 8a illustrates a plot of a possible pressure differential versus time for a pneumatic system. As seen in FIG. 8a, at cycle interval time (T), the pressure differentials may be +10 and −13 psi (pounds per square inch) on the open/close positions (resulting in a pressure range 801 of approximately 23 psi). The lowest performance point may be the cycle interval time when the differential pressure difference between the pressure open and pressure closed is the lowest (i.e., when (abs(pressure open)+abs(pressure closed)) is at a minimum for the pressure data. In the case shown in FIG. 8a, there is a noticeable dip in pressures for the open and closed position at cycle interval time (T).

At 709, a valve duty cycle to compensate for the pressure bias may be determined. In the pressure data shown in FIG. 8a, at cycle interval time (T), the pressure bias appears to be approximately 3 psi (associated with the −13 psi reading over the +10 psi reading). A valve duty cycle that would result in approximately centering the pressure differential (e.g., aimed at obtaining open/close pressure values of approximately +11.5 psi and −11.5 psi at cycle interval time (T)) may be determined. Determining the valve duty cycle to center the pressure differentials at the lowest performance point of the pneumatic system may insure that the pneumatic system has sufficient pressure to operate in both the open and closed positions at its lowest performance point (the valve duty cycle may also result in improved performance at the other operating points of the pneumatic system). While several examples herein determine a valve duty cycle around the lowest performance point, a valve duty cycle may also be determined using other points in the pressure data. Determining a valve duty cycle may be calculated as follows:

New valve duty cycle=Previous valve duty cycle+
(((abs(open pressure)−abs(closed pressure))/2)*
(valve duty cycle delta/differential pressure
change delta))

Where open pressure and closed pressure are taken at a time of lowest performance for the pneumatic system (e.g., time T in the current example) and where abs( ) represents the absolute valve. In some embodiments, the valve duty cycle to pressure differential adjustment ratio may be determined mathematically or through trial and error. For example, the ratio may be 1% (valve duty cycle delta) to 0.86 psi (differential pressure change delta).

In the current example:

New valve duty cycle=50%+(((13 psi−10 psi)/2)*
(1%/0.86 psi))

New valve duty cycle=50%+(1.5 psi*(1%/0.86 psi))

New valve duty cycle=50%+1.744%=51.744%

Thus, the pressure on the close side (currently +10 psi) may be increased to 11.5 psi with the new valve duty cycle of 51.744% (10 psi+1.744%*(0.86 psi/1%)=11.5 psi) and the open side may be shifted to −11.5 psi (−13 psi+1.744%* (0.86 psi/1%)=−11.5 psi). In some embodiments, the valve duty cycle may be rounded to a nearest increment (e.g., rounded to 51.5% if rounding to nearest increments of 0.5%).

At 711, the pneumatic system may be programmed with the new valve duty cycle. For example, the DIP switches (which may be physically accessible switches with on/off or 1/0 options) may be set in an on/off sequence that will produce a voltage corresponding to the determined valve duty cycle. In some embodiments, the new valve duty cycle may be computed by the surgical console and/or entered into a graphical user interface of the surgical console.

At 713, the pneumatic system may be operated again (e.g., 5 to 10 seconds). During the pneumatic system operation, pressure data for the run may be detected through the pressure sensors. In some embodiments, the pneumatic system may be discontinued after the initial run and then run again for another set amount of time (e.g., 5 to 10 seconds) before taking the pressure data. In some embodiments, a wait time (e.g., 5 to 10 seconds) may be applied between pneumatic system runs.

Figure 8B:
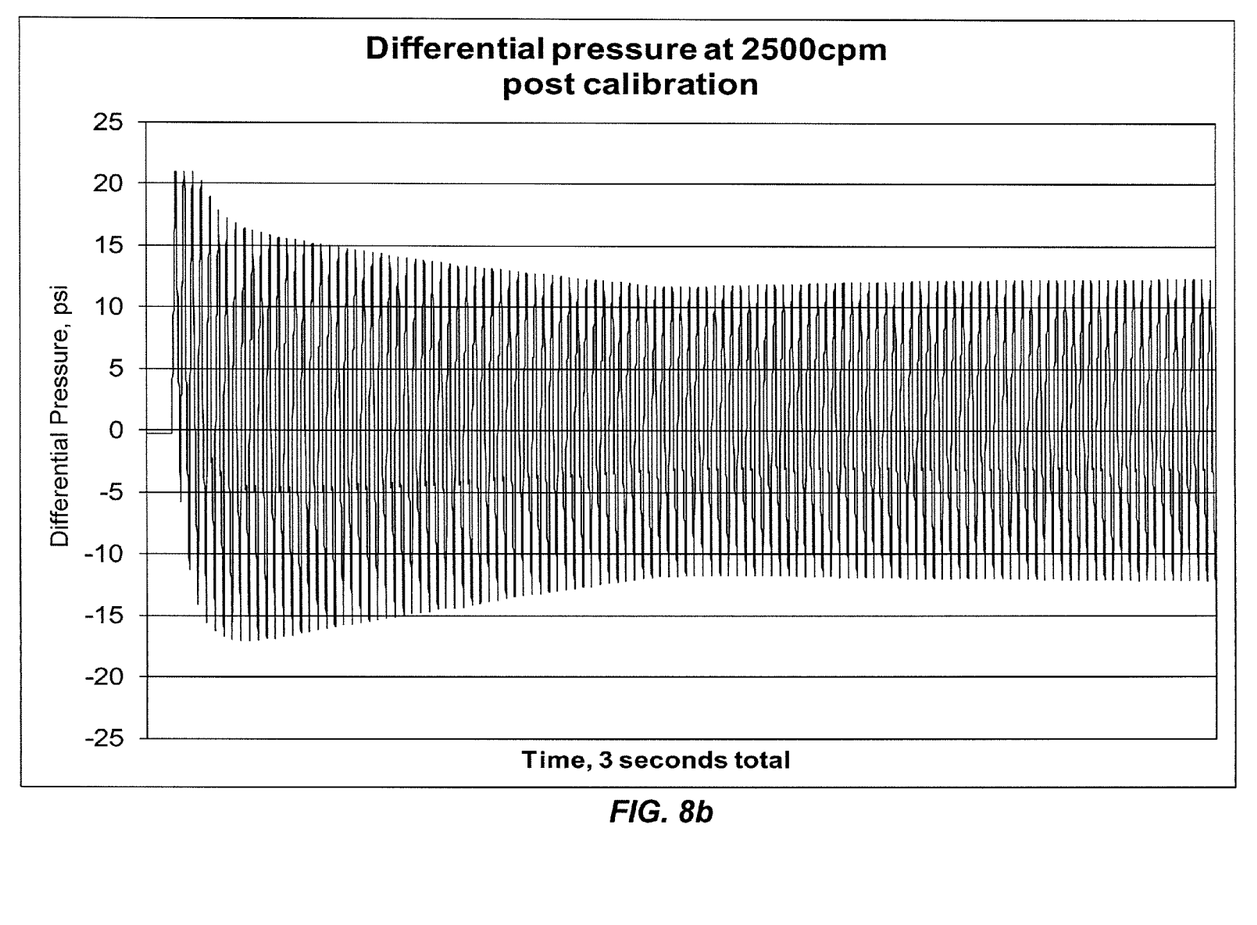

At 715, pressure differentials and pressure range between the open/close valve positions may be determined again. FIG. 8b illustrates a possible plot of pressure data after applying the new valve duty cycle. As seen in FIG. 8b, the pressure differential may now be approximately centered around 0 psi such that the pressure differential in the closed position is approximately 11.5 psi at the lowest performance point for the closed position and approximately −11.5 psi for the lowest performance point in the open position.

At 717, pressure differentials, pressure range, and/or pressure bias may be compared to acceptable limits. In some embodiments, the pressure differentials (e.g., in the corrected case the differentials are approximately +11.5 psi and −11.5 psi as seen in FIG. 8b), may be compared to a predetermined threshold for operation (e.g., the absolute values of the differentials may be compared to a threshold of approximately 10 psi). In the corrected case shown in FIG. 8b, the differential pressures (absolute values for comparison purposes) are greater than the threshold of 10 psi. In some embodiments, a pressure bias (the pressure difference between the two channels) may also be determined and compared to a predetermined acceptable limit. For example, the pressure bias may equal to abs(closed pressure)−abs (open pressure). After calibration, a predetermined acceptable pressure bias limit of 1 psi may be used (other pressure bias may also be used depending on the pneumatic system calibration). As another example, the total pressure range (abs(open pressure)+abs(closed pressure)) may be compared to a predetermined acceptable limit (e.g., a minimum 21.6 psi of range). In some embodiments, the total pressure range at a point of lowest performance for the pneumatic system may be compared to an acceptable total pressure range to determine if the pneumatic system has a leak or restriction. For example, if the total pressure range is <21.6 psi, there may be a leakage or restriction in the system. Other total pressure range may also be used (different pneumatic system configurations may operate at different pressures and pressure ranges). If the total pressure range at the lowest performance point does not meet the minimum acceptable limit, the valve may be replaced and/or the pneumatic system may be checked. Also, if edges of pressure wave form are not smooth, but are wavy or have shifts, or are not expanding on both sides after the minimum performance points, the valve may need to be replaced.

At 719, if the total pressure range or pressure bias is out of the acceptable range, a new valve duty cycle may be used. In some embodiments, the new valve duty cycle may be recalculated. For example:

New valve duty cycle=Previous valve duty cycle+
(((abs(open pressure)−abs(closed pressure))/2)*
(valve duty cycle delta/pressure change delta))

Where open pressure and closed pressure may be differential pressures at a time of lowest performance for the pneumatic system. In some embodiments, instead of using the equation, a valve duty cycle that is one increment above or below the previous valve duty cycle may be tried. If the previous closed pressure needs to be increased (to reduce the pressure bias toward the open position), the valve duty cycle may be increased to the next increment (e.g., from 51% to 51.5%) or vice versa. In some embodiments, the new valve duty cycle may be determined by the surgical console and/or entered into a graphical user interface of the surgical console. In some embodiments, DIP switches may be set to correspond to the new determined valve duty cycle. The new valve duty cycle may then be tested (e.g., by performing elements 713 to 719)

At 721, if the valve has been tested more than a set number of times (e.g., twice) and the total pressure range or pressure bias is still out of the acceptable range, a different valve/module may be installed. In some embodiments, additional rounds of determining a new valve duty cycle (or the DIP switches may be moved to correspond to another valve duty cycle above or below the previous one) may be performed.

At 723, if the total pressure range and the pressure bias from 717 are within the acceptable ranges, the calibration process may be concluded. The surgical console may use the determined valve duty cycle. In some embodiments, the DIP switches and resistance network may relay the desired valve duty cycle (through a characteristic voltage) to the system console during operation. For example, a voltage from the resister network may be converted into a digital count through an analog/digital converter 509. The digital count may be processed by software executing on the surgical console and a corresponding valve duty cycle may be determined and used to modify the valve performance. In some embodiments, the calibration process may be performed multiple times to insure repeatability of the calibration results with the determined valve duty cycle.

In some embodiments, the vitrectomy system may include one or more processors (e.g., controller 300). The controller 300 may include single processing devices or a plurality of processing devices. Such a processing device may be a microprocessor, controller (which may be a micro-controller), digital signal processor, microcomputer, central processing unit, field programmable gate array, programmable logic device, state machine, logic circuitry, control circuitry, analog circuitry, digital circuitry, and/or any device that manipulates signals (analog and/or digital) based on operational instructions. Memory coupled to and/or embedded in the processors may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processors implement one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory may store, and the processor may execute, operational instructions corresponding to at least some of the elements illustrated and described in association with, for example, FIG. 7.

Various modifications may be made to the presented embodiments by a person of ordinary skill in the art. It is intended that the present specification and examples be considered as exemplary only with a true scope and spirit of the invention being indicated by the following claims and equivalents thereof.

What is claimed is:

1. A method for operating a surgical console, comprising:
providing pressurized gas, through a valve, alternately to each of a first port and a second port to drive a pneumatic tool coupled to the surgical console;
controlling valve open and close times according to a valve duty cycle, wherein the valve open time corresponds to a time to open the first port and wherein the valve close time corresponds to a time for closing the first port, wherein closing the first port coincides with opening the second port such that the pressurized gas is being directed by the valve either through the first port or the second port;
calculating the valve duty cycle by:
(a) analyzing operating pressure data for open and closed valve positions, and
(b) determining the valve duty cycle to provide the valve open time and valve close time that will result in open and closed operating differential pressures above a predetermined threshold.

2. The method for operating the surgical console of claim 1, wherein the valve is a four-way solenoid valve.

3. The method for operating the surgical console of claim 1, further comprising coupling the pneumatic tool to the first and second ports of the surgical console, wherein the pneumatic tool is a vitrectomy cutter.

4. The method for operating the surgical console of claim 1, wherein a total valve time equals the valve open time plus the valve close time for a valve cycle, and wherein the valve duty cycle is a percentage of the total valve time the valve directs gas through the first port.

5. The method for operating the surgical console of claim 1, further comprising storing the valve duty cycle on a memory on the surgical console.

6. The method for operating the surgical console of claim 5, wherein storing the valve duty cycle on the memory comprises storing the valve duty cycle on a plurality of DIP switches (dual in-line package switches), wherein the DIP switches are configurable to combine one or more of a plurality of resistors in a resistor network such that upon applying an input voltage to the resistor network, an output voltage of the resistor network is indicative of the valve duty cycle.

7. The method for operating the surgical console of claim 6, further comprising converting the output voltage to a digital value using an analog to digital converter, wherein software executing on the surgical console is operable to determine a valve duty cycle that corresponds to the digital value through a look-up table.

8. The method for operating the surgical console of claim 1, wherein analyzing the operating pressure data comprises analyzing an open pressure and a closed pressure for the first and second port during a lowest performance point of a set of measured pressures for the surgical console.

9. A method of calibrating a surgical pneumatic system, comprising:
  operating a pneumatic system comprising a pneumatic valve configured to cycle between an open position and a closed position wherein pressurized gas is directed at a first port when the valve is in the open position and wherein the pressurized gas is directed at a second port when the valve is in the closed position;
  measuring pressures output by the pneumatic valve, wherein the measured pressure data comprises an open differential pressure corresponding to a differential pressure between the first port and the second port during the open position and a closed differential pressure corresponding to a differential pressure between the first port and the second port during the closed position; and
  calculating a valve duty cycle by:
  (a) analyzing operating pressure data for open and closed valve positions, and
  (b) determining the valve duty cycle to provide a valve open time and a valve close time that will result in open and closed operating differential pressures above a predetermined threshold.

10. The method of claim 9, further comprising storing the valve duty cycle on a plurality of DIP switches (dual in-line package switches), wherein the DIP switches are configurable to combine one or more of a plurality of resistors in a resistor network such that upon applying an input voltage to the resistor network, an output voltage of the resistor network is indicative of the valve duty cycle.

11. The method of claim 9, wherein an open pressure and a closed pressure for the first port are taken during a lowest performance point during the measured pressures for the pneumatic system.

12. The method of claim 9, wherein determining the valve duty cycle comprises determining a new valve duty cycle and wherein the method further comprises using the new valve duty cycle to modify a valve open position timing.

13. The method of claim 9 further comprising:
  operating the pneumatic system and measuring pressures output by the pneumatic valve;
  calculating a total pressure range, wherein the total pressure range is equal to a sum of absolute values of an open pressure and a closed pressure; and
  determining if the total pressure range is greater than a predetermined total pressure range limit.

14. The method of claim 12, further comprising:
  operating the pneumatic system and measuring pressures output by the pneumatic valve;
  calculating a pressure bias, wherein the pressure bias is about equal to (absolute value of closed pressure)−(absolute value of open pressure);
  determining if the pressure bias is less than a predetermined pressure bias limit.

15. The method of claim 14, wherein the open pressure and the closed pressure are measured during a lowest performance point.

16. The method of claim 15, wherein the lowest performance point is the point when the pressure difference between the open pressure and closed pressure is the lowest such that ((absolute value of pressure open)+(absolute value of pressure closed)) is at a minimum for the measured pressure data.

* * * * *